United States Patent
Myoga

[11] Patent Number: 5,904,662
[45] Date of Patent: May 18, 1999

[54] CERVICAL COLLAR

[76] Inventor: Maki Myoga, 8649 SW. Shawn Pl., Portland, Oreg. 97223

[21] Appl. No.: 08/419,495

[22] Filed: Apr. 10, 1995

[51] Int. Cl.$^6$ ...................................................... A61F 5/00
[52] U.S. Cl. .............................................................. 602/18
[58] Field of Search .................................. 602/17, 18, 19; 128/DIG. 23

[56] References Cited

U.S. PATENT DOCUMENTS

| | | | |
|---|---|---|---|
| 2,828,736 | 1/1958 | Monfardini | 602/18 |
| 2,911,970 | 11/1959 | Bartels | 602/18 |
| 3,374,785 | 3/1968 | Gaylord, Jr. . | |
| 3,810,466 | 5/1974 | Rogers | 602/18 |
| 3,850,164 | 11/1974 | Hare . | |
| 3,916,884 | 11/1975 | Attenburrow | 602/18 |
| 3,921,626 | 11/1975 | Neel . | |
| 3,964,474 | 6/1976 | Fox . | |
| 4,232,663 | 11/1980 | Newton . | |
| 4,325,363 | 4/1982 | Berkeley | 602/18 |
| 4,819,622 | 4/1989 | Taylor et al. . | |
| 4,987,891 | 1/1991 | Gaylord, Jr. et al. . | |
| 5,060,637 | 10/1991 | Schmid et al. . | |
| 5,230,698 | 7/1993 | Garth | 602/18 |
| 5,275,581 | 1/1994 | Bender . | |
| 5,403,266 | 4/1995 | Bragg et al. | 602/18 X |

*Primary Examiner*—Richard J. Apley
*Assistant Examiner*—Kim M. Lee
*Attorney, Agent, or Firm*—Olson & Olson

[57] ABSTRACT

A cervical collar is formed by folding a blank of resilient foamed elastomer or synthetic resin along a longitudinal centerline and enclosing the folded blank in a stretch fabric cover. The rounded, folded edge contributes increased deflection resistance through the vertical dimension of the folded blank and is configured for placement against the jaw areas of a wearer. Openings in the blank allow installation of plugs or air bladders to adjust the vertical dimension and deflection resistance of the collar to accommodate application to necks of various heights and strengths.

16 Claims, 5 Drawing Sheets

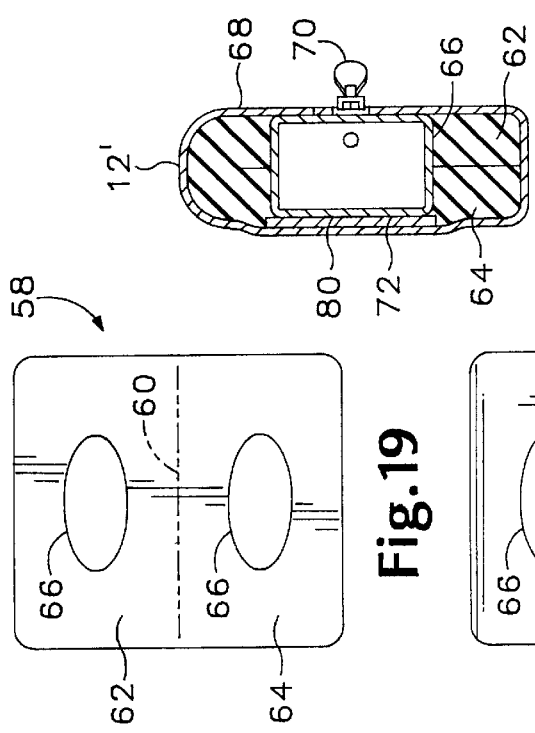
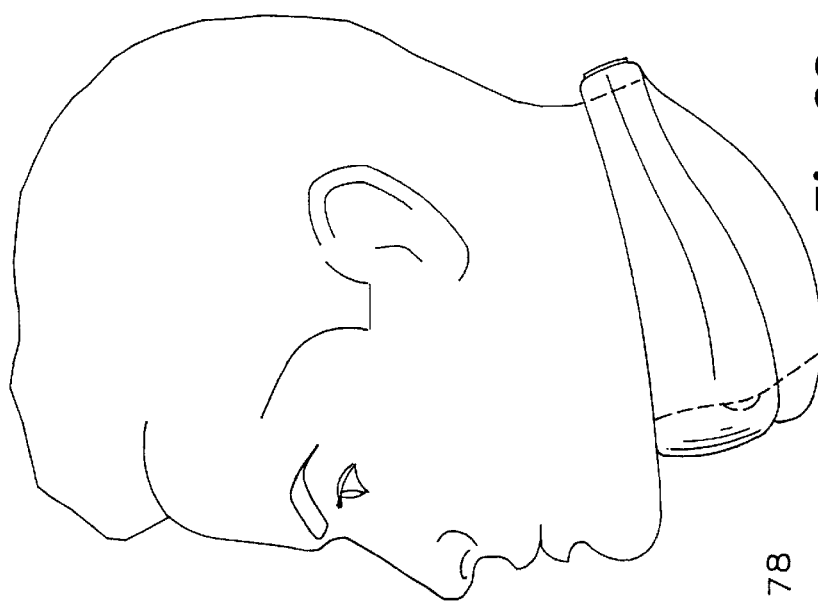
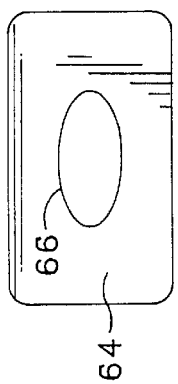
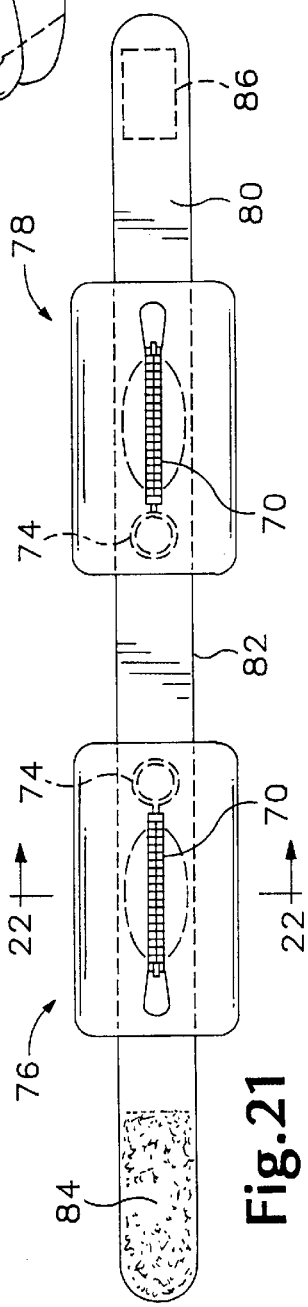
Fig.19 Fig.20 Fig.22 Fig.21 Fig.23

CERVICAL COLLAR

BACKGROUND OF THE INVENTION

This invention relates to cervical collars, and more particularly to a cervical collar of improved support and comfort characteristics for use primarily in the workplace, home and while traveling, and to a method for making the same.

There are two basic forms of cervical collars. One is a costly, multi-component, rigid structure for use in medical emergency situations that require immobilization of the head and neck by medically trained personnel. The second form of cervical collar is an inexpensive, one-piece, resilient strip of foamed rubber or synthetic resin that can be wrapped and secured about the neck by the wearer to provide support for the head while permitting a limited degree of freedom of movement of the head. The present invention relates to cervical collars of this second form.

Workplace tasks, such as a computer work station, require the operator to position the hands for manipulating a keyboard and to otherwise assume a relatively fixed posture of the body and head in front of the display. This static condition results in muscular fatique and consequent discomfort in the neck and shoulders. The use of a cervical collar of the second form described above, even for a few minutes periodically through the work hours, overcomes the muscular fatigue and results beneficially in improved comfort and consequent productivity.

One-piece cervical collars of the second form described above have been provided heretofore. Since they have utilized conventional foamed synthetic resins, typically foamed polyurethane resin, they have had to incorporate some means to increase the density of the foam, or otherwise decrease the resilience thereof, sufficiently to provide increased deflection resistance to adequately support the head and neck.

One such means for decreasing the resilience of the foamed synthetic resin, described in U.S. Pat. No. 3,374,785 is to re-form the foamed material into small cubes and thereafter bond the cubes together with a binder. This bonded mixture then is heated to a softened condition and forced into a mold and cured to form a shaped core material of increased density. The core material is covered with a porous fabric and mating fasteners are secured to the opposite ends of the core for attaching the collar about the neck. This elaborate procedure contributes adversely to excessive manufacturing cost.

Another means for decreasing the resilience of foamed synthetic resin is to provide one or more reinforcement components of non-foamed synthetic resin which also support the foamed resin collar in annular shape. This construction is described in U.S. Pat. No. 3,964,474. The two piece construction described therein is characterized by excessive manufacturing cost and is rather uncomfortable to wear while working.

Still another means for providing a cervical collar of suitable head and neck-supporting capability is to form the collar of a corrugated plastic material in which the corrugations extend parallel to the axial dimension of the neck. Such a collar is described in U.S. Pat. No. 5,060,637. A similar construction, formed with an axially extending splint assembly fastened to the outer side of a soft foamed resin collar, is disclosed in U.S. Pat. No. 5,275,581. These structures also are rather expensive to manufacture and are rather uncomfortable to wear while working.

Other such cervical collars utilize specially foamed synthetic resins of higher than normal density to achieve the required head and neck support. Illustrative of these are U.S. Pat. Nos. 3,850,164 and 4,987,891. This high density foamed resin is costly to manufacture and it presents an unsatisfactory degree of discomfort to the wearer.

SUMMARY OF THE INVENTION

The cervical collar of this invention utilizes the increased deflection resistance and contour of the rounded edge of a folded sheet of foamed elastomer or synthetic resin to provide effective and comfortable support for the jaw areas of the face of a wearer. Openings may be provided in the jaw area of the folded sheet to removably receive plugs or pressurized air bladders to provide variable deflection resistance in the vertical direction of the folded sheet, whereby to enhance the support for the jaw areas, while simultaneously adjusting the vertical length of the collar to accommodate necks of various lengths.

It is the principal objective of this invention to provide a cervical collar which avoids the aforementioned limitations and disadvantages of prior one-piece cervical collars.

Another objective of this invention is to provide a cervical collar of the class described which is adjustable in vertical dimension and deflection resistance as well as circumference to accommodate use by person's of various facial and neck dimensions.

A further objective of this invention is the provision of a cervical collar of the class described which affords the required deflection resistance in the jaw areas of a wearer while minimizing interference with normal activity of the chin and throat.

Still another objective of this invention is to provide a cervical collar of the class described which is of simplified and economical construction.

A further objective of this invention is the provision of a method of making a cervical collar of the class described.

The foregoing and other objects and advantages of this invention will appear from the following detailed description, taken in connection with the accompanying drawings of preferred embodiments.

BRIEF DESCRIPTION OF THE DRAWINGS

FIG. 19 is a plan view of a flat sheet of foamed material in the form of a contoured blank for forming a fifth cervical collar embodiment of this invention.

FIG. 20 is a plan view of the folded blank of FIG. 19.

FIG. 21 is a plan view of a pair of the folded structures of FIG. 20 enclosed in elastic stretch fabric covers and supported on an elongated strap to complete the fifth cervical collar embodiment.

FIG. 22 is a sectional view taken on the line 22—22 in FIG. 21.

FIG. 23 is a profile view of a human head showing applied about the neck thereof a cervical collar embodying the features of this invention.

DESCRIPTION OF THE PREFERRED EMBODIMENTS

Figure 1:
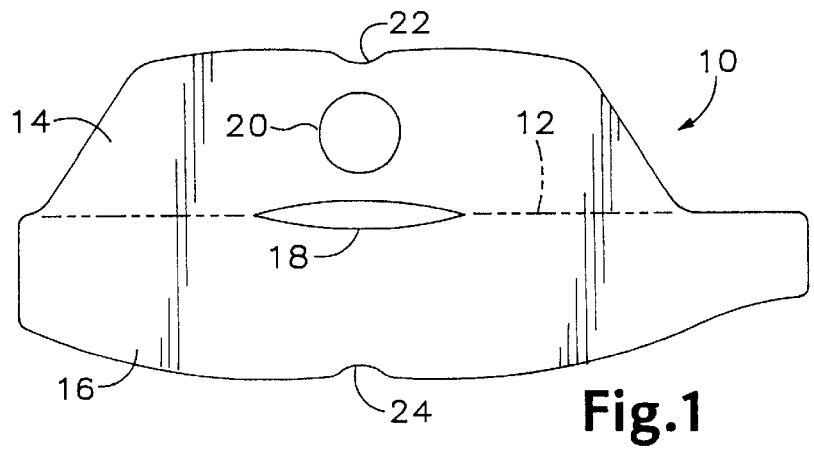
FIG. 1 is a plan view of a flat sheet of foamed material in the form of a contoured blank for forming a first cervical collar embodiment of this invention.
Figure 2:
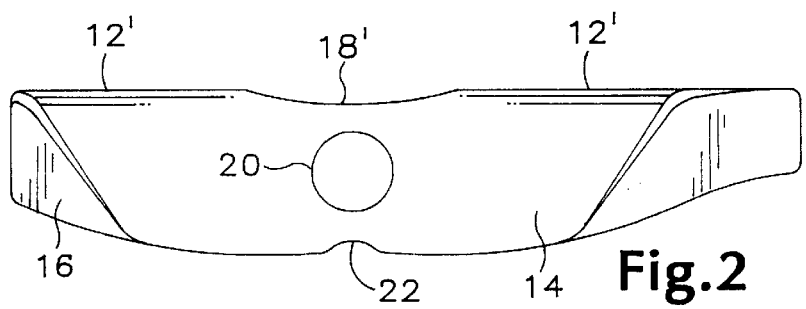
FIG. 2 is a plan view of the folded blank of FIG. 1.

The basic concept of this invention is illustrated in FIGS. 1–5 of the drawings. Therein is shown a blank 10 formed of a sheet of flexible, resilient foamed elastomer or synthetic resin shaped to be folded on a central longitudinal line 12 to provide an inner section 14 and an outer section 16. The inner section is arranged to confront the neck of a wearer and the outer section is arranged to face forwardly of the wearer. Typically, the sheet is about one-half inch thick, although other thicknesses may be chosen as desired.

An oval or other desired shaped opening 18 in the blank 10 is centered on the fold line 12. Thus, when the blank is folded and fitted about the neck of a wearer, the opening 18 forms a pair of registering recesses 18' configured to receive the underside of the chin of the wearer with a minimum of upward pressure.

A substantially circular opening 20 is provided in the central portion of the inner section 14, such that when the blank is folded and fitted about the neck of a wearer, the opening registers with the Adams apple projection of the larynx. This relief of pressure on the larynx contributes beneficially to optimizing comfort of the wearer.

A pair of arcuate or otherwise curved notches 22 and 24 are provided in the outward longitudinal edges of the inner and outer sections 14 and 16, respectively, in line with the openings 18 and 20. These notches register with each other when the blank is folded, and provide protection against crushing of a tie knot when the collar is fitted about the neck of a wearer.

Figure 4:
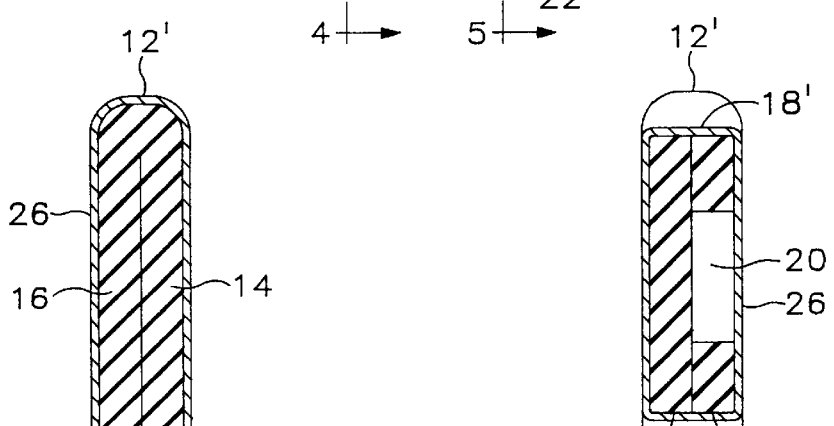
FIG. 4 is a sectional view taken on the line 4—4 in FIG. 3.
Figure 5:
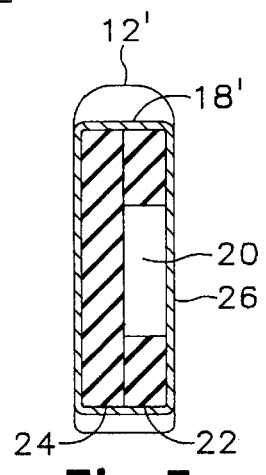
FIG. 5 is a sectional view taken on the line 5—5 in FIG. 3.
Figure 6:
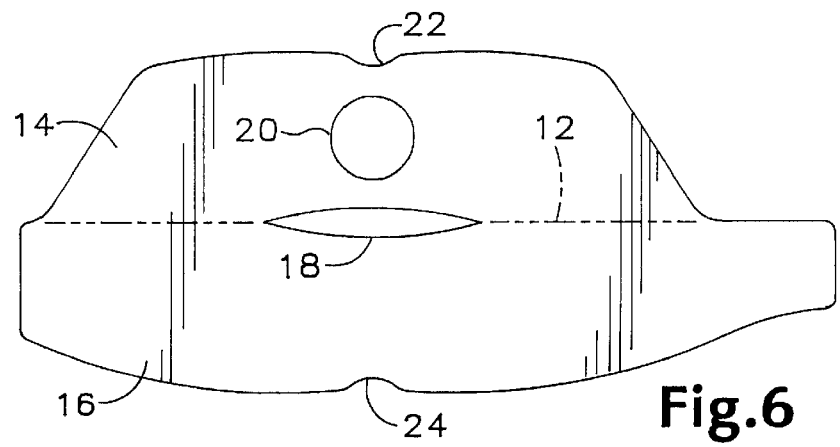
FIG. 6 is a plan view of a flat sheet of foamed material in the form of a contoured blank for forming a second cervical collar embodiment of this invention.
Figure 7:
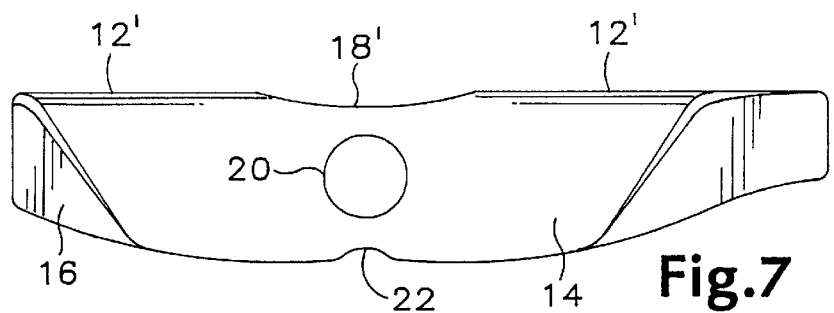
FIG. 7 is a plan view of the folded blank of FIG. 6.
Figure 8:
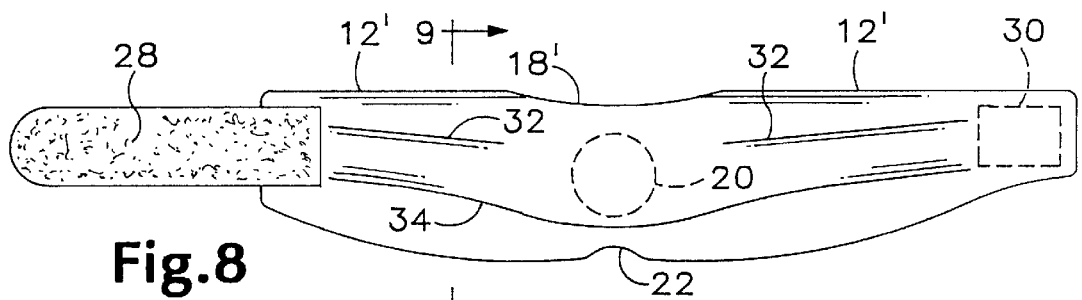
FIG. 8 is a plan view of the folded structure of FIG. 7 enclosed in an elastic stretch fabric cover to complete the second cervical collar embodiment.
Figure 9:
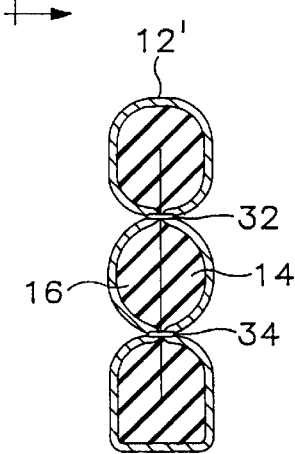
FIG. 9 is a sectional view taken on the line 9—9 in FIG. 8.
Figure 10:
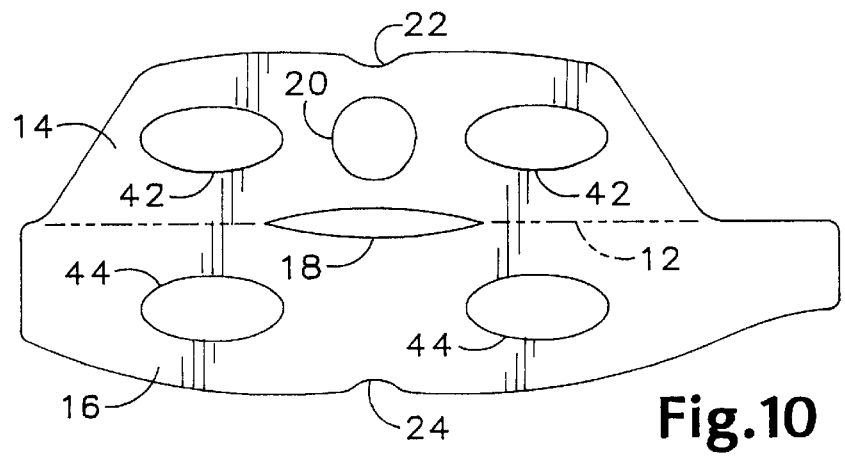
FIG. 10 is a plan view of a flat sheet of foamed material in the form of a contoured blank for forming a third cervical collar embodiment of this invention.
Figure 11:
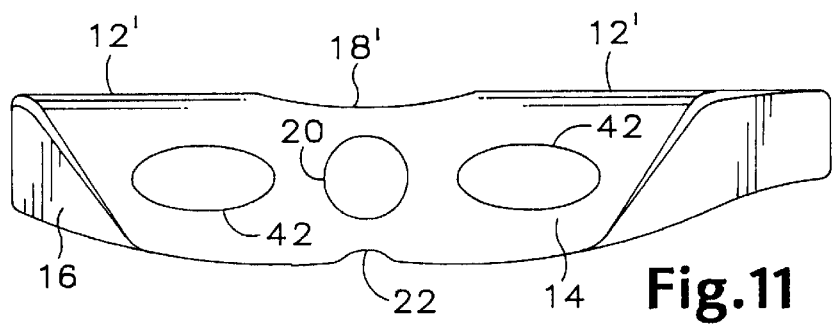
FIG. 11 is a plan view of the folded blank of FIG. 10.

When the blank is folded, as illustrated in FIG. 4, the abutting surfaces preferably are bonded together, as by adhesive, to prevent the halves of the blank from bowing outwardly. Such a condition not only decreases the vertical deflection resistance, but also presents an unattractive outward bulging and an uncomfortable inward bulging and pressing against the neck of the wearer.

The folded blank is slipped into or otherwise enclosed in a cover 26 of soft, elastic, stretchable fabric, such as Lycra. The elasticity of the fabric allows it to follow the contours of the recesses 18' and notches 22 and 24, and presents minimum resistance across the opening 20.

Means is provided for securing the opposite ends of the collar detachably about the neck of a wearer. Although there are many types of fasteners suitable for this purpose, it is preferred to utilize a conventional burr-type fastener, known as "VELCRO", to accommodate a range of adjustability for necks of various thicknesses. Thus, a strap 28 containing the hook components of a "VELCRO" fastener is secured, as by stitching, to one end of the cover 26, and a strip 30 of companion loop components is secured to the opposite end of the cover.

Of significant importance in this invention is the provision of the closed, rounded edge 12' created by folding the blank 10 along the fold line 12. Although the foamed blank generally is sufficiently soft and flexible to provide comfort to the neck area of a wearer, the free edges of the folded blank have insufficient deflection resistance for proper support of the jaws. The folded edge 12' contributes sufficient additional resistance to deflection to provide effective support for the jaws in the areas rearwardly of the chin.

Figure 3:
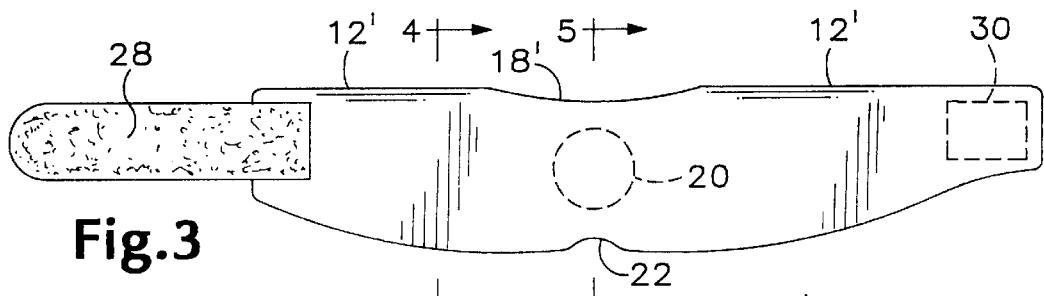
FIG. 3 is a plan view of the folded structure of FIG. 2 enclosed in an elastic stretch fabric cover to complete the first cervical embodiment.

In use, the assembled collar shown in FIG. 3 is wrapped around the neck of a wearer, from the front, and the opposite ends secured together at the back of the neck by the Velcro fastener. The recess 18' receives the chin for comfortable movement and the rounded folded edges 12' to the opposite sides of the recess press resiliently upward against the confronting areas of the jaws to provide effective support for the head.

A variety of sizes of blanks 10 may be provided to accommodate use by wearers having necks of various lengths and girth. The blanks generally are made wider to provide the folded blanks with various vertical dimensions, i.e. between the recess 18' and notches 22 and 24.

It has been found that a wearer need only use the collar in this manner for a short time interval, for example 15 minutes or so, to obtain significant relief from the neck tension and shoulder fatigue incident to the maintenance of such a relatively static or immobile position as prevails at a computer work station.

This invention contemplates the provision of a cervical collar having variable resistance to deflection through its vertical dimension, i.e., between the rounded edge 12' and the opposite, free edges containing the notches 22 and 24, than is provided by the embodiment illustrated in FIGS. 1–5. Increased resistance to deflection may be required by a wearer having a stronger neck, and may be provided by the embodiment shown in FIGS. 6–9. Thus, the embodiment of FIGS. 1–5 is modified by the addition of the vertically spaced, longitudinally extending lines of stitchings 32 and 34 which extend through the thickness of the folded blank and cover 26 in the areas at opposite sides of the recess 18 which register with the jaws of a wearer. The stitchings, or other suitable form of bonding, compress the folded blank into upper, middle and bottom segments 36, 38 and 40, respectively, of greater deflection resistance. The stitchings also allow increased lateral flexing of the segments and consequent increased freedom of mobility of the neck and head. Thus, while the increased deflection resistance of the segments provides the required support in the jaw area, the increased mobility allows greater freedom of movement of the neck and head, for increased comfort of use.

Figure 12:
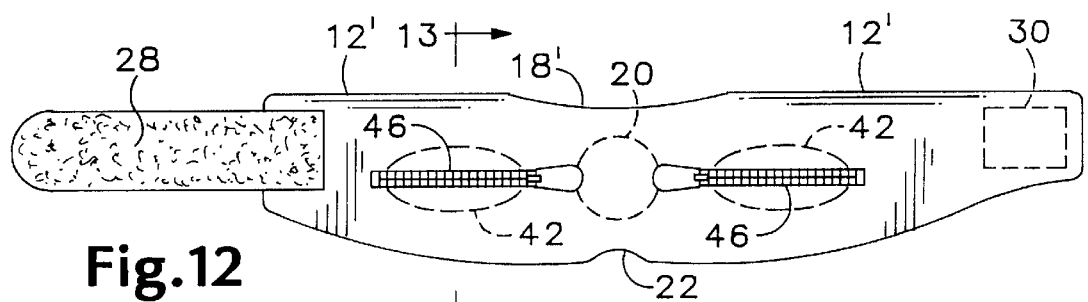
FIG. 12 is a plan view of the folded structure of FIG. 11 enclosed in an elastic stretch fabric cover to complete the third cervical collar embodiment.

In another embodiment of this invention, increased deflection resistance is provided while, if desired, simultaneously increasing the vertical dimension of the folded blank to accommodate necks of various lengths. Referring to FIGS. 10–14, the inner and outer sections 14 and 16 of the blank 10 are provided with openings 42 and 44 disposed laterally outward to opposite sides of the oval opening 18 and arranged for registration when the blank is folded to the condition shown in FIG. 11. The folded blank then is enclosed in cover 26 (FIG. 12).

The inner side of the cover is provided with a pair of laterally spaced slits, preferably closed removably by slide fasteners 46 or other form of closure, registering with the openings 42 and 44. By opening the slits, the openings 42 and 44 are exposed for the insertion of plugs 48 into the openings 42 and 44. The plugs preferably are made of foamed material having a density and deflection resistance greater than the foamed material of the blank 10, to increase the deflection resistance of the collar in the rounded, folded areas 12' registering with the jaws of a wearer.

Figure 13:
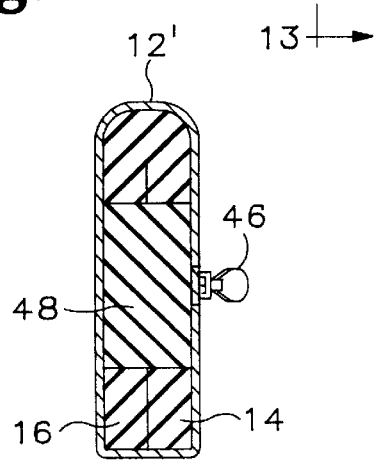
FIG. 13 is a sectional view taken on the line 13—13 in FIG. 12 showing the chamber filled with a plug of foamed material of greater density and deflection resistance than that of the foamed sheet.

The plugs also may be made larger in vertical dimension than the openings 42 and 44, in order to effect increasing the vertical dimension of the folded blank. This is illustrated in FIG. 13 and it accommodates use of the collar on necks of diverse lengths. If preferred, the plugs may be made the same size as the openings in order to increase the deflection resistance without increasing the vertical dimension of the folded blank. Alternatively, the plugs may be made of foamed material having a density less than the foamed material of the blank 10, to reduce the vertical deflection resistance below that afforded by plugs 48 and above that afforded by the empty openings 42 and 44.

Figure 14:
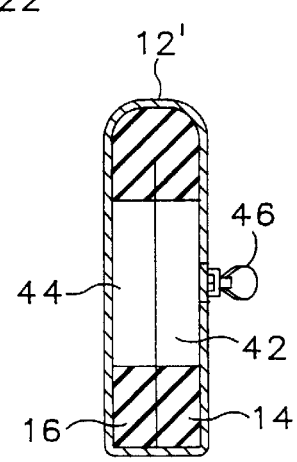
FIG. 14 is a sectional view similar to FIG. 13 but showing the internal chamber empty.
Figure 15:
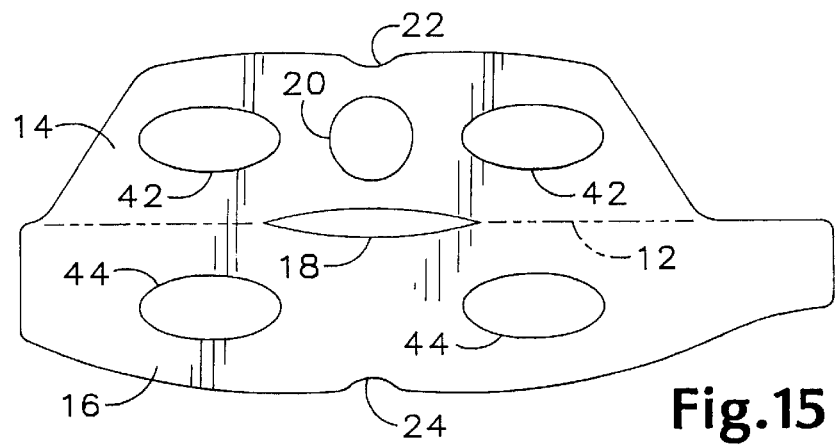
FIG. 15 is a plan view of a flat sheet of foamed material in the form of a contoured blank for forming a fourth cervical collar embodiment of this invention.
Figure 16:
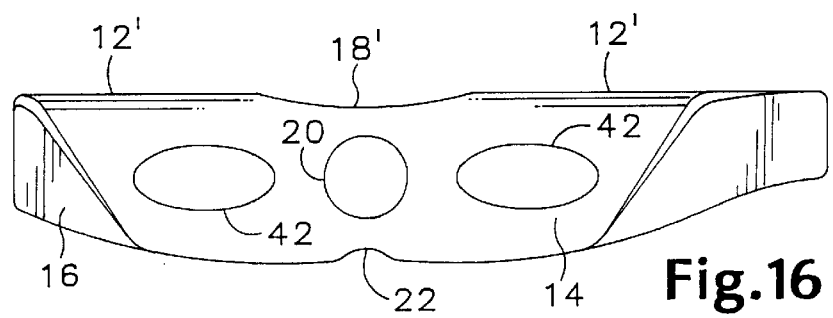
FIG. 16 is a plan view of the folded blank of FIG. 15 with interconnected air bladders contained within openings in the folded blank.
Figure 17:
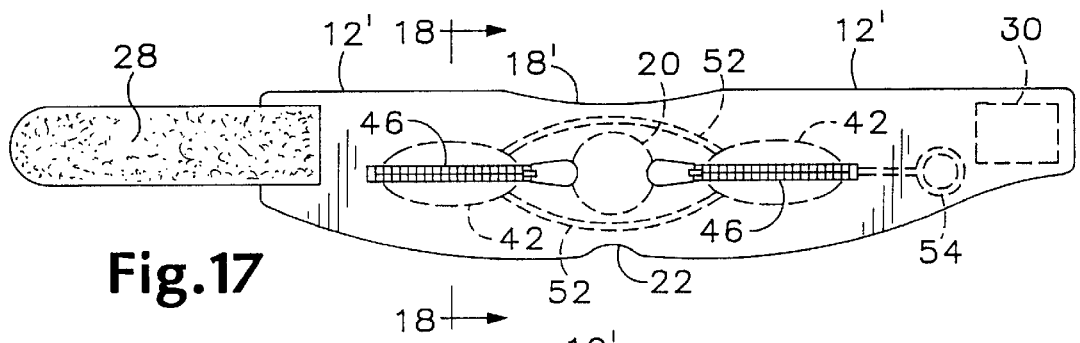
FIG. 17 is a plan view of the folded structure of FIG. 16 enclosed in an elastic stretch fabric cover to complete the fourth cervical collar embodiment.
Figure 18:
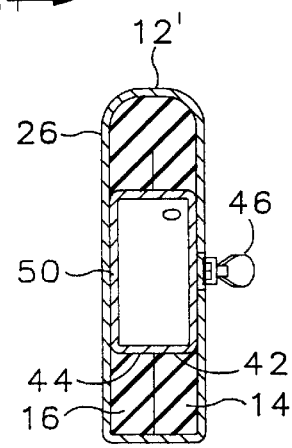
FIG. 18 is a sectional view taken on the line 18—18 in FIG. 17.

It is to be observed from FIG. 14 that when the openings 42 and 44 are left empty, the vertical deflection resistance and vertical dimension of the folded blank is reduced below that of the folded blank of FIG. 13. This degree of deflection resistance may be suitable for certain applications, and the empty condition may also apply to the embodiments described hereinafter.

In the embodiment of FIGS. 15–18 the plugs 48 of the last described embodiment are replaced with air bladders 50 interconnected by one or more tubes 52. Means for introducing air under pressure into the air bladders is provided by a finger-operated flexible air pump bulb 54 of well-known design, connected to one of the air bladders. In the alternative, a length of tubing may be connected to one of the air bladders 50 for insertion in the mouth for blowing air under pressure into the bladders, after which the tubing is sealed by a stopper. In any event, the air bladders may be inflated with air under pressure to a magnitude which provides the deflection resistance and increased vertical height of the collar desired for selected use.

The embodiment illustrated in FIGS. 19–22 differs from the preceding embodiments in the substitution of a pair of blanks 58 for the single blank 10. Each blank is foldable on a longitudinal centerline 60, forming inner and outer segments 62 and 64, respectively. An opening 66 in each of these segments registers one with the other when the blank is folded, after which each folded blank is enclosed in an elastic stretch fabric cover 68. In the preferred embodiment illustrated, each cover is provided with an elongated slit removably closed by a slide fastener 70. Opening of the slide fastener gains access to the openings 66 for insertion of an air bladder 72 with air pump 74, or for insertion of a plug of the type described in connection with FIG. 13.

The pair of fabric-enclosed, folded blanks form a pair of neck pads 76 and 78 and are supported on an elongated strap 80 which is threaded through the space between the outer segment 64 and the confronting surface of the cover 68. The pair of neck pads thus are separately adjustable along the strap 80 for optimum positioning for supporting the jaws of a wearer. The space 82 between the pads receive the chin of the wearer for maximum mobility and comfort.

One end section 84 of the strap 80 is provided with the hook component of a burr-type, or VELCRO fastener, and the opposite end section 86 of the strap is provided with the companion loop component of the fastener. The collar thus may be secured about the neck of a wearer and the pads 76 and 78 slid along the strap 80 to most effective support positions. If desired, the deflection resistance and vertical dimension of each pad may be varied by corresponding variation in air pressure supplied to the air bladders 72.

From the foregoing, it will be appreciated that this invention provides a cervical collar of versatile utility. Although it may be employed to immobilize the neck and head for a variety of orthopedic emergencies, it has particular application in the relief of muscular fatigue and consequent discomfort in the neck and shoulders commonly experienced in such workplace tasks as computer operations. The collar is small in size, attractive in appearance and easily and quickly applied to and removed from the neck for short term use in relieving muscular fatigue.

It will be apparent to those skilled in the art that various changes may be made in the size, shape, type, number and arrangement of parts described hereinbefore without departing from the spirit of this invention and the scope of the appended claims.

I claim:

1. A cervical collar for encircling the neck and supporting the underside of the jaw areas of a wearer, the collar comprising an elongated resilient folded sheet of a foamed material selected from the group consisting of foamed elastomer and foamed synthetic resin folded on a longitudinal centerline to form an upper elongated jaw-supporting, transversely rounded, longitudinal fold edge of increased vertical deflection resistance providing means along said folded longitudinal centerline for receiving the chin and the jaw areas of a wearer, and elongated inner and outer sheet sections having opposite longitudinal ends, a stretch fabric cover enclosing the elongated folded sheet, and fastener means on the cover for securing the opposite longitudinal ends of the cover-enclosed, elongated, folded sheet together.

2. The cervical collar of claim 1 wherein the elongated inner sheet section of the elongated sheet includes an opening forming a cavity adapted to receive the projecting Adam's apple of the larynx of a wearer when said elongated sheet is folded along said longitudinal centerline, the cavity being hidden from view by the outer sheet section when the collar is installed about the neck of a wearer.

3. The cervical collar of claim 1 including a pair of lines of stitching extending through the elongated folded sheet and cover in the jaw areas thereof and spaced apart between the rounded longitudinal fold edge and the edge opposite thereto, the upper line of stitching extending from adjacent the longitudinal ends of the folded sheet longitudinally inward and terminating at spaced apart positions adjacent the central portion of the folded sheet, the lower line of stitching extending from adjacent one longitudinal end of the folded sheet to adjacent the opposite longitudinal end of the folded sheet, the lines of stitching drawing the folded sheet and cover inwardly to compress the foamed folded sheet and increase the vertical deflection resistance of the folded sheet in the jaw areas of the fold edge.

4. A cervical collar for encircling the neck and supporting the jaw areas of a wearer, the collar comprising an elongated resilient folded sheet of a foamed material selected from the group consisting of foamed elastomer and foamed synthetic resin folded on a longitudinal centerline to provide an elongated jaw-supporting transversely rounded longitudinal fold edge and elongated inner and outer sheet sections having opposite longitudinal ends, the elongated sheet including an opening extending partially along said longitudinal fold centerline, the opening forming a recess adapted to receive the chin of a wearer when the said elongated sheet is folded along said longitudinal centerline, the elongated inner sheet section of the elongated sheet including an opening forming a cavity adapted to receive the projecting Adam's apple of the larynx of a wearer when said elongated sheet is folded along said longitudinal centerline, the elongated inner and outer sheet sections of the elongated sheet including a pair of laterally spaced openings arranged for registration when said elongated sheet is folded along said longitudinal centerline, registering openings being located in the areas of the elongated inner and outer sheet sections that register with the jaw areas of a wearer, means insertable in the registering openings in the elongated inner and outer sheet sections for varying the vertical deflection resistance of said sections and for adjusting the vertical dimension of the folded sheet, a stretch fabric cover enclosing the elongated folded sheet, and fastener means on the cover for securing said opposite longitudinal ends together.

5. A cervical collar for encircling the neck and supporting the jaw areas of a wearer, the collar comprising an elongated resilient folded sheet of a foamed material selected from the group consisting of foamed elastomer and foamed synthetic resin folded on a longitudinal centerline to provide an elongated jaw-supporting, transversely rounded, longitudinal fold edge and elongated inner and outer sheet sections having opposite longitudinal ends and including a pair of laterally spaced openings arranged for registration when the said elongated sheet is folded along said longitudinal centerline, the registering openings being located in the areas of the elongated inner and outer sheet sections that register with the jaw areas of a wearer, the registering openings in the said elongated inner and outer sheet sections providing for varying the vertical deflection resistance of said sheet sections, a stretch fabric cover enclosing the elongated folded sheet, and fastener means on the cover for securing the opposite longitudinal ends of the cover-enclosed, elongated, folded sheet together.

6. The cervical collar of claim 5 including plugs of foamed material insertable in said registering openings and having deflection resistance different from that of the foamed sheet.

7. The cervical collar of claim 5 including means insertable in said registering openings capable of adjusting the vertical dimension of the folded sheet.

8. The cervical collar of claim 7 including bladders insertable in said registering openings and capable of being inflated with air under pressure.

9. A cervical collar for encircling the neck and supporting the jaw areas of a wearer, the collar comprising a pair of elongated resilient folded sheets of a foamed material selected from the group consisting of foamed elastomer and foamed synthetic resin each folded on a longitudinal centerline to provide a jaw-supporting, transversely rounded, longitudinal fold edge and inner and outer sheet sections, the inner and outer sheet sections of each folded sheet including openings arranged for registration when the sheet is folded, the registering openings in said inner and outer sheet sections providing for varying the vertical deflection resistance of said sheet sections, a stretch fabric cover enclosing each folded sheet, an elongated strap having opposite ends and extending slidably through the pair of covered folded sheets between the cover and outer sheet section of each folded sheet for adjusting the pair of folded and covered sheets along the length of said strap for positioning in registry with the jaw areas of a wearer, and fastener means on the opposite end portions of the strap for releasably securing said end portions together.

10. The cervical collar of claim 9 including plugs of foamed material insertable in said registering openings and having deflection resistance different from that of the foamed sheet.

11. The cervical collar of claim 9 including bladders insertable in said registering openings and capable of being inflated with air under pressure.

12. The cervical collar of claim 9 including means insertable in said registering openings capable of adjusting the vertical dimension of said folded sheet.

13. A cervical collar for encircling the neck and supporting the underside of the jaw areas of a wearer, the collar comprising a pair of elongated, resilient, folded sheets of a foamed material selected from the group consisting of foamed elastomer and foamed synthetic resin, each folded on a longitudinal centerline to provide an elongated jaw-supporting, transversely rounded, longitudinal fold edge of increased vertical deflection resistance for engaging the underside of a jaw area of a wearer, and elongated inner and outer sheet sections, a stretch fabric cover enclosing each folded sheet, an elongated strap having opposite ends and extending slidably through the pair of covered folded sheets between the cover and outer sheet section of each folded sheet for adjusting the pair of folded and covered sheets along the length of said strap for positioning in registry with the jaw areas of a wearer, and fastener means on the opposite end portions of the strap for releasably securing said end portions together.

14. A cervical collar for encircling the neck and supporting the underside of the jaw areas of a wearer, the collar comprising an elongated, resilient, folded sheet of a foamed material selected from the group consisting of foamed elastomer and foamed synthetic resin folded on a longitudinal centerline to provide an elongated jaw-supporting, transversely rounded, longitudinal fold edge of increased vertical deflection resistance for engaging the undersides of the jaw areas of a wearer, and elongated inner and outer sheet sections having opposite longitudinal ends, the elongated sheet prior to folding including an opening extending partially along said longitudinal fold centerline centrally between said opposite longitudinal ends, said opening forming a recess in said rounded fold edge adapted to receive the chin of a wearer when said elongated sheet is folded along said longitudinal centerline, a stretch fabric cover enclosing the elongated folded sheet, and fastener means on the cover for securing the opposite longitudinal ends of the cover-enclosed, elongated, folded sheet together.

15. A cervical collar for encircling the neck and supporting the underside of the jaw areas of a wearer, the collar comprising an elongated, resilient, folded sheet of a foamed material selected from the group consisting of foamed elastomer and foamed synthetic resin folded on a longitudinal centerline to provide an elongated jaw-supporting, transversely rounded, longitudinal fold edge of increased vertical deflection resistance for engaging the undersides of the jaw areas of a wearer, and elongated inner and outer sheet sections having opposite longitudinal ends, a stretch fabric cover enclosing the elongated folded sheet, fastener means on the cover for securing the opposite longitudinal ends of the cover-enclosed, elongated, folded sheet together, and a pair of lines of stitching extending through the elongated folded sheet and cover in the jaw areas thereof and spaced apart between the rounded longitudinal fold edge and the edge opposite thereto, the upper line of stitching extending from adjacent the longitudinal ends of the folded sheet longitudinally inward and terminating at spaced apart positions adjacent the central portion of the folded sheet, the lower line of stitching extending from adjacent one longitudinal end of the fold sheet to adjacent the opposite longitudinal end of the fold sheet, the lines of stitching drawing the folded sheet and cover inwardly to compress the foamed folded sheet and increase the vertical deflection resistance of the folded sheet in the jaw areas of the fold edge.

16. A cervical collar for encircling the neck and supporting the underside of the jaw areas of a wearer, the collar comprising an elongated resilient folded sheet of a foamed material selected from the group consisting of foamed elastomer and foamed synthetic resin folded on a longitudinal centerline to form an upper elongated jaw-supporting, transversely rounded, longitudinal fold edge of increased vertical deflection resistance, and elongated inner and outer sheet sections having opposite longitudinal ends, the elongated sheet prior to folding including an opening extending partially along said longitudinal fold centerline centrally between said opposite longitudinal ends, said opening forming a recess in said means for receiving the chin of a wearer when said elongated sheet is folded along said longitudinal centerline, a stretch fabric cover enclosing the elongated folded sheet, and fastener means on the cover for securing the opposite ends of the cover-enclosed, elongated, folded sheet together.

* * * * *